United States Patent [19]

Papa

[11] 4,214,000
[45] Jul. 22, 1980

[54] ZINC SALT OF ALL-TRANS-RETINOIC ACID FOR THE TREATMENT OF ACNE

[75] Inventor: Christopher M. Papa, Colts Neck, N.J.

[73] Assignee: Johnson & Johnson, New Brunswick, N.J.

[21] Appl. No.: 955,997

[22] Filed: Oct. 30, 1978

[51] Int. Cl.² .................. A61K 31/315; C07F 3/06
[52] U.S. Cl. .......................... 424/289; 260/429.9; 424/344
[58] Field of Search .............. 424/289; 260/429.9, 260/410.9 V; 562/510

[56] References Cited

U.S. PATENT DOCUMENTS

| 3,729,568 | 4/1973 | Kligman | 424/318 |
| 3,856,941 | 12/1974 | Turner | 424/145 |
| 3,906,108 | 9/1975 | Felty | 424/318 |
| 3,949,072 | 4/1976 | Tenta | 424/145 |
| 4,039,681 | 8/1977 | Abdel-Monem | 424/289 |
| 4,053,630 | 10/1977 | Yu et al. | 424/289 |

FOREIGN PATENT DOCUMENTS 1476717 6/1977 United Kingdom .

OTHER PUBLICATIONS

Chemical Abstracts 76:158354x (1972).

Primary Examiner—Leonard Schenkman
Attorney, Agent, or Firm—Irving Newman

[57] ABSTRACT

A zinc salt of retinoic acid has been prepared and found to have significant anti-acne activity, similar to that of retinoic acid, but with less of a tendency to cause flaking or irritation at anti-acne effective concentrations.

29 Claims, No Drawings

ZINC SALT OF ALL-TRANS-RETINOIC ACID FOR THE TREATMENT OF ACNE

TECHNICAL FIELD

This invention relates to a zinc salt of all-trans-retinoic acid and to topical pharmaceutical compositions for the treatment of acne that contain said zinc salt as the active ingredient.

BACKGROUND ART

Acne vulgaris is a dermatological disorder prevalent in adolescence. It appears most commonly on the face and trunk of the patient. The basic lesion of acne is the comedo or blackhead of a pilosebaceous follicle. In its mildest form, only few comedones are present, but in its severe form, a large number of severe, persistent comedones are present. Permanent scarring is frequently a consequence of the severe form of acne.

Acne occurs when there is a filling up of the follicle with a rather tough keratinous material. This impaction of horny material is the whitehead and blackhead. As a result of bacterial growth in these horny impactions, the follicle ruptures, initiating the inflammatory phase of the disease, which takes the form of pustules, papules, cysts and nodules.

A variety of methods has been used for the treatment of acne, including the use of peeling agents, hormone therapy for female patients, antibacterial therapy, general surgical skin planing and the topical use of vitamin A acid (all-trans-retinoic acid, tretinoin) as well as of benzoyl peroxide.

DISCLOSURE OF INVENTION

A zinc salt of all-trans-retinoic acid has been synthesized, having the theoretical structural formula:

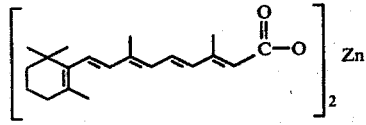

It has, moreover, been discovered that said zinc salt of all-trans-retinoic acid has the unexpected property of having anti-acne efficacy similar to that of retinoic acid but with a reduced propensity to cause skin flaking or irritation at dosage levels that are effective to combat acne.

Accordingly, the present invention provides a new composition of matter, a zinc salt of all-trans-retinoic acid, as well as a topical composition for the treatment of acne comprising a therapeutically effective concentration of such zinc salt of all-trans-retinoic acid in a pharmaceutically acceptable topical vehicle compatible therewith. In another aspect, the invention comprises a method of treating acne by applying such composition to the affected site at regular intervals, preferably once or twice daily.

Best Mode For Carrying Out The Invention

A suitable method for preparing a zinc salt of retinoic acid in accordance with the present invention, as well as indicia for confirming its identity, are set forth in Example 1 below.

While the topical compositions of the present invention may take any convenient topical form, such as lotion, cream or gel, provided the vehicle is compatible with the zinc salt of retinoic acid and is otherwise pharmaceutically acceptable, for cosmetic reasons as well as enhanced efficacy the presently preferred form is an alcoholic gel formulation. Other suitable vehicles will be apparent to those skilled in the art of formulating topical retinoid-containing pharmaceutical compositions, as will be apparent from the discussion hereinafter. General guidelines for suitable formulation vehicle components are set forth below (all percentages are by weight, based on the total weight of the final composition, unless otherwise indicated).

In general, the preferred gel formulations of the present invention comprise a therapeutically effective amount of a zinc salt of all-trans-retinoic acid; an organic solvent for said zinc salt, preferably one selected from the group consisting of ethanol (absolute or 95% by volume ethyl alcohol), isopropanol, proylene glycol and combinations thereof; a suitable antioxidant, preferably one selected from the group consisting of butylated hydroxytoluene (BHT), butylated hydroxyanisole (BHA), butylated hydroxyanisole (BHA), ascorbic acid (Vitamin C), propyl gallate, and $\alpha$-tocopherol (Vitamin E); and a suitable gelling agent, preferably one selected from the group consisting of (1) an acidic carboxy vinyl polymer of high molecular weight, such as those available under the trade names Carbopol 934 and Carbopol 940, preferably neutralized with a suitable alkaline material such as potassium hydroxide or an organic amine, (2) hydroxyethylcellulose and (3) hydroxypropyl cellulose. Other conventionally used ingredients may be added, if desired, such as dyes, perfumes, sunscreens, antimicrobials and topical corticosteroids.

A general formula encompassing gel formulations within the scope of the present invention is set forth below.

| General Gel Formula in % w/w | |
|---|---|
| Zinc salt of all-trans-retinoic acid | 0.001–0.5 |
| Antioxidant(s) | 0.01–0.1 |
| Gelling agent(s) | 0.5–5.0 |
| Dye(s) and/or perfume oil(s) | 0.0–0.75 |
| Sunscreen(s) | 0.0–2.5 |
| Topical corticosteroid | 0.0–2.0 |
| Antimicrobial(s) | 0.0–3.0 |
| Organic solvent | q.s. ad 100.0 |

While the compositions of the present invention are described herein primarily as suitable for use in treating acne, it will be understood that these compositions are effective generally for treating dermatological conditions where tretinoin has been indicated. Moreover, as indicated above, and as will be apparent to those skilled in the art, any topical vehicle that is suitable for use with tretinoin will, in general, also be suitable for a zinc salt of retinoic acid. In this connection, reference may be had to U.S. Pat. Nos. 3,729,568 and 3,906,108, as well as British Pat. No. 1,476,717 for tretinoin formulations in which a zinc salt of all-trans-retinoic acid could suitably be substituted for tretinoin to prepare topical compositions in accordance with the present invention.

A suitable cream emulsion formulation in accordance with the present invention generally comprises from about 0.005 to about 0.5 weight % of a zinc salt of all-trans-retinoic acid; from about 0.1 to about 1.0 weight % of a suitable stabilizer, preferably xanthan gum; from about 1% to about 10% by weight of an emulsifier, preferably a non-ionic emulsifier; from about 15 to about 50 weight % of a combination of at least one normally liquid and at least one normally solid hydrophobic material selected from the fatty alcohols and fatty acid esters wherein the fatty acid moiety has from about 12 to about 20 carbon atoms, and pharmaceutical grades of waxes and hydrocarbons (liquid and solid); between about 0.05 and 0.75 weight % of a preservative which prevents bacterial growth in the cream; and from about 0.01 to about 1.0 weight % of an antioxidant, the balance being water. Optionally, minor amounts of such commonly used cosmetic adjuvants, additives and the like as humectants, sequestering agents, dyes, perfume oils and sunscreens may also be included.

Moreover, it is also contemplated that the compositions of the invention may contain, in combination with the zinc salt of all-trans-retinoic acid, such topically active medicaments as the anti-inflammatory corticosteroids.

While generally a mixture of a liquid and a solid hydrophobic material is used in the cream formulations, this is not essential, particularly where a semisolid such as petrolatum is employed. A preferred range for the concentration of zinc salt of retinoic acid in the cream formulation is from about 0.02 to about 0.3% by weight, from about 0.05 to about 0.15 weight % being particularly preferred.

Suitable liquid vehicles are pharmaceutically acceptable solvents that are compatible with a zinc salt of retinoic acid, such as, ethanol, isopropanol, propylene glycol, liquid polyethylene glycols (e.g., polyethylene glycol 400), liquid polypropylene glycol, and mixtures of one or more of the foregoing simple alcohols wth each other or with one or more of the foregoing glycols. Generally, as in the case of the gels and creams discussed above, an antioxidant will be included, and other optional ingredients as discussed above may also be included. The concentration range of zinc salt of retinoic acid in the liquid vehicles is, in general, from about 0.005% to about 0.5% by weight, with a more preferred range being from about 0.05% to about 0.2% by weight.

While the concentration of zinc salt of retinoic acid in the gel compositions of the present invention may be as low as 0.001 or 0.0025 weight %, in cream or solution form the minimum concentration will generally be about 0.005%. A broad range for zinc salt of retinoic acid concentration in the compositions of the present invention is thus from about 0.001% to about 0.5% by weight. A more preferred range for this concentration in the liquid and cream compositions is from about 0.05% to about 0.2%, while for the gel a preferred range is from about 0.005 to about 0.1 weight %, from about 0.01 to about 0.05 weight % being particularly preferred.

The antioxidants which may be used in the compositions of the present invention are those which are not reactive with the gelling agents, zinc salt of retinoic acid or other components of the formulations and are safe for human topical use. It is preferred to employ from about 0.025 to about 0.1 weight % of an antioxidant selected from the group consisting of butylated hydroxytoluene (BHT), butylated hydroxyanisole (BHA), ascorbic acid (Vitamin C), propyl gallate, and α-tocopherol (Vitamin E), although other antioxidants may be used provided they satisfy the above criteria.

The gelling agents employed in the gel compositions of the present invention are those capable of being solvated or those which can be modified to be capable of being solvated in the solvents utilized in these compositions and which are commonly used in pharmaceutical preparations for topical applications. It is preferred to use amounts of from about 0.5 to about 5.0 weight % of a gelling agent selected from the group consisting of hydroxyethylcellulose having a viscosity of from about 3,500 to about 50,000 cps. when a 2 percent aqueous solution is measured at 20° C. using a Brookfield Viscometer, Model LVF, with Spindle #30 at 30 RPM. (available under the trade name Natrosol from Hercules Powder Co. Inc., Wilmington, Delaware); hydroxypropyl cellulose having a molecular weight of from about 100,000 to about 1,000,000 (available under the trade name Klucel from Hercules Powder Co. Inc.); and an acidic carboxy vinyl polymer of high moledular weight (such as those available under the name Carbopol 934 and Carbopol 940 from B.F. Goodrich Chemical Co., Cleveland, Ohio), preferably neutralized with a suitable alkaline neutralizing agent such as potassium hydroxide, β-alanine or diisopropanol amine.

While many organic solvents could be used to solubilize the zinc salt of retinoic acid in the gel formulations, ethanol, isopropanol, propylene glycol and mixtures therof are particularly preferred for reasons related to toxicity, irritation and quality of product made therewith. As indicated previously, the solvents form the largest part by weight of the gel compositions of the present invention and are generally present in amounts of from about 84 weight % to about 99 weight %.

The compositions of the invention may be prepared by various methods practiced and well known in the art. In general, the formula amount of antioxidant is dissolved in the solvent, followed by the addition and subsequent solvation of the formula amount of tretinoin.

In the case of gels, the formula amount of gelling agent is added in small quantities under low shear agitation until solvation occurs and the mixture gels. When an acidic carboxy vinyl polymer of high molecular weight such as Carbopol 934 or Carbopol 940 is used as the gelling agent, the neutralization, if desired, is accomplished by adding the neutralizing agent after the last portion of the acidic carboxy vinyl polymer is added to the mixture and sufficient amount of time allowed for its dispersion. Low shear agitation continues until solvation occurs and the gel is formed.

The formulation procedure preferably should take place at room temperature, i.e., at about 25° C. If desired, additional materials, such as dyes, perfumes, sunscreens, and corticosteroids may be incorporated into the formulations by adding and mixing them with the solvent (prior to the addition of the gelling agent in the case of gel formulations).

There is no criticality in the particular surfactant employed in the cream compositions of this invention. In general, however, non-ionic surfactants are preferred. Of these, the polyoxyalkylene fatty acid esters, more particularly, the polyoxyalkylene stearates, are most commonly employed. These surfactants are well known in the art. Suitable examples include; polyoxyethylene 25 oxypropylene stearate, polyoxyl 40 stearate, polyethylene glycol 400 monostearate, and polyethylene glycol 600 monostearate. It is preferred to employ from about 2 to about 5 weight % of the surfactant.

The hydrophobic (fatty) materials which can be used in the cream compositions of this invention are well known to those skilled in the art. They include the fatty acids, fatty alcohols and fatty acid esters, wherein the fatty acid moiety has from about 12 to about 20 carbon atoms, such as, for example, stearyl alcohol, stearic acid, isopropyl myristate and cetyl alcohol; as well as pharmaceutical grades of beeswax, including White wax, sperm wax, lanolin, mineral oil, etc. As previously indicated, cream formulations in accordance with this invention generally should contain at least one liquid and at least one solid ingredient from this class of materials.

Suitable preservatives for the compositions of this invention include benzyl alcohol, methyl paraben, propyl paraben, sorbic acid, etc. While as little as 0.05 weight % of these materials may be present, it is preferred that the composition contain from about 0.2 to about 0.5 weight % thereof.

The foregoing materials and the criteria for their selection are well known in the art, as is the case with respect to the humectants, sequestering agents, dyes, antioxidants, perfumes, sunscreens and other ingredients which may optionally be included in the compositions of this invention. Typical examples of such additives are propylene glycol, glycerin, sorbitol, butylated hydroxytoluene, citric acid, $\alpha$-tocopherol, ethylenediamine tetraacetic acid and metal salts thereof, sodium hexametaphosphate and amyl paradimethylaminobenzoate.

Examples of anti-inflammatory corticosteroids which may be incorporated in the compositions of the present invention include hydrocortisone, betamethasone benzoate, desfluorotriamcinolone, triamcinolone acetonide, dexamethasone, dexamethasone acetate, flumethasone pivalate, flumethasone valerate and deprodone propionate. When present in the compositions of the present invention, their concentration is generally in the range of from about 0.025 to about 2.0 weight %.

In use, the compositions of the invention are applied topically to the area to be treated or protected, at regular intervals, as needed, generally from about 7 to about 21 times per week. The duration of the treatment will depend upon the nature and severity of the condition to be treated as well as the frequency of application of the composition. In general, however, improvement is noticeable within the first week or two.

The following examples are presented to further illustrate the present invention without thereby limiting the scope thereof.

EXAMPLE 1

Preparation of a Zinc Salt of all-trans-retinoic Acid

All-trans-retinoic acid (12.00 grams; 0.0399 mole) was stirred magnetically in a 400-ml. beaker with 60 ml. of distilled water. The suspension was neutralized with 63.2 ml. of 0.633 N methanolic potassium hydroxide. After addition of the base, the solution was stirred for five minutes. The potassium retinoate solution was then filtered through paper to remove any particles of acid which do not dissolve.

A 250-ml. flask was fitted with a mechanical stirrer, a dropping funnel and a nitrogen inlet tube. In the flask was placed a solution of 6.00 grams of zinc nitrate flakes (Mallinckrodt Analytical Reagent, No. 8808, $Zn(NO_3)_2 \cdot xH_2O$) in 30 ml. of distilled water and 30 ml. of methanol.

The zinc nitrate solution was stirred under a stream of nitrogen while the filtered potassium retinoate solution was added dropwise from the dropping funnel during about 15 minutes. The reaction mixture becomes progressively thicker due to precipitation of a yellow zinc retinoate salt. The slurry was stirred for 30 minutes after all the potassium retinoate was added. Nitrogen flow was continued throughout the stirring period. The precipitate was filtered with suction on a 3.25-inch-diameter, coarse sintered glass funnel. It was washed on the filter by reslurrying with distilled water. This hydrated zinc retinoate salt was spread in a crystallizing dish and vacuum dried in a foil-covered desiccator until it weighed between 20 and 30 grams. The usual drying cycle is 4 to 5 hours at 0.30 mm. Hg(oil pump), followed by overnight drying under house vacuum (about 250 mm. Hg).

The hydrated zinc salt was then dissolved in 60 ml. of Reagent Grade tetrahydrofuran by stirring it magnetically for a few minutes. The somewhat turbid solution was filtered through paper into a 1000-ml. beaker. While the filtered solution was stirred, 600 ml. of distilled water were added to it in a thin stream during about 10 minutes. The zinc salt precipitated as a sticky orange gum. The beaker was then chilled in ice for about 10 minutes during which the gum hardened considerably. Stirring of the slurry was then continued for one hour longer while the beaker was cooled in the ice bath. The precipitate, which had now hardened, was filtered on sintered glass with suction, washed with water and vacuum dried in a foil-covered desiccator. A drying cycle of five hours on the house vacuum, followed by overnight drying at 0.30 mm. on the oil pump, resulted in a friable product which weighs between 10.8 and 11.2 grams. This was easily crushed to a fine powder with mortar and pestle.

The composition of this zinc salt of retinoic acid falls within the following limits (in weight percent):

C, 64.0 to 66.0 H, 7.5 to 7.9 Zn, 7.1 to 8.5

When U.V. absorptivity of this salt is measured in chloroform, it exhibits a maximum at about 360 nm.

EXAMPLE 2

| Ingredients | 0.1% Gel (% w/w) |
| --- | --- |
| Zinc salt of retinoic acid | 0.1 |
| Butylated hydroxytoluene, N.F. | 0.05 |
| Hydroxypropyl cellulose | 3.0 |
| Specially denatured alcohol #40 (190 proof) q.s. ad | 100.0 |

EXAMPLE 3

| Ingredients | 0.2% Gel (% w/w) |
| --- | --- |
| Zinc salt of retinoic acid | 0.2 |
| Butylated hydroxytoluene, N.F. | 0.05 |
| Hydroxypropyl cellulose | 3.0 |
| Specially denatured alcohol #40 (190 proof) q.s. ad | 100.0 |

EXAMPLE 4

| Ingredients | 0.5% Gel (% w/w) |
| --- | --- |
| Zinc salt of retinoic acid | 0.5 |
| Butylated hydroxytoluene, N.F. | 0.05 |
| Hydroxypropyl cellulose | 3.0 |
| Specially denatured alcohol | |

-continued

0.5% Gel

| Ingredients | (% w/w) |
|---|---|
| #40 (190 proof) q.s. ad | 100.0 |

EXAMPLE 5

0.2% Gel

| Ingredients | (% w/w) |
|---|---|
| Zinc salt of retinoic acid | 0.2 |
| Butylated hydroxytoluene, N.F. | 0.1 |
| Hydroxypropyl cellulose | 3.0 |
| Specially denatured alcohol #40 (190 proof) q.s. ad | 100.0 |

EXAMPLE 6

0.05% Gel

| Ingredients | (% w/w) |
|---|---|
| Zinc salt of retinoic acid | 0.05 |
| Butylated hydroxytoluene, N.F. | 0.1 |
| Hydroxypropyl cellulose | 3.0 |
| Specially denatured alcohol #40 (190 proof) q.s. ad | 100.0 |

EXAMPLE 7

0.01% Gel

| Ingredients | (% w/w) |
|---|---|
| Zinc salt of retinoic acid | 0.01 |
| Butylated hydroxytoluene, N.F. | 0.1 |
| Hydroxypropyl cellulose | 3.0 |
| Specially denatured alcohol #40 (190 proof) q.s. ad | 100.0 |

EXAMPLE 8

0.005% Gel

| Ingredients | (% w/w) |
|---|---|
| Zinc salt of retinoic acid | 0.005 |
| Butylated hydroxytoluene, N.F. | 0.1 |
| Hydroxypropyl cellulose | 3.0 |
| Specially denatured alcohol, #40 (190 proof) q.s. ad | 100.0 |

EXAMPLE 9

0.2% Solution

| Ingredients | (% w/w) |
|---|---|
| Zinc salt of retinoic acid | 0.2 |
| Butylated hydroxytoluene, N.F. | 0.1 |
| Propylene glycol | 50.0 |
| Specially denatured alcohol, 200° q.s. ad | 100.0 |

EXAMPLE 10

0.02% Solution

| Ingredients | (% w/w) |
|---|---|
| Zinc Salt of retinoic acid | 0.02 |
| Butylated hydroxytoluene, N.F. | 0.1 |
| Propylene glycol | 30.0 |
| Specially denatured alcohol, 200° q.s. ad | 100.0 |

EXAMPLE 11

0.2% Solution

| Ingredients | (% w/w) |
|---|---|
| Zinc salt of retinoic acid | 0.2 |
| Butylated hydroxytoluene, N.F. | 0.1 |
| Propylene glycol | 10.0 |
| Specially denatured alcohol, 200° q.s. ad | 100.0 |

EXAMPLE 12

0.1% Solution

| Ingredients | (% w/w) |
|---|---|
| Zinc salt of retinoic acid | 0.1 |
| Butylated hydroxytoluene, N.F. | 0.1 |
| Polyethylene glycol 400, U.S.P. | 50.0 |
| Alcohol, SDA 40, q.s. ad | 100.0 |

EXAMPLE 13

0.1% Solution

| Ingredients | (% w/w) |
|---|---|
| Zinc salt of retinoic acid | 0.1 |
| Butylated hydroxytoluene, N.F. | 0.1 |
| Polyethylene glycol, U.S.P. | 30.0 |
| Alcohol, 200°, q.s. ad | 100.0 |

EXAMPLE 14

0.1% Solution

| Ingredients | (% w/w) |
|---|---|
| Zinc salt of retinoic acid | 0.1 |
| Butylated hydroxytoluene, N.F. | 0.1 |
| Glycerin | 10.0 |
| Alcohol, SDA 40, q.s. ad | 100.0 |

EXAMPLE 15

0.05% Solution

| Ingredients | (% w/w) |
|---|---|
| Zinc salt of retinoic acid | 0.05 |
| Butylated hydroxytoluene, N.F. | 0.1 |
| Propylene glycol, U.S.P. | 50.0 |
| Alcohol, 200°, q.s. ad | 100.0 |

EXAMPLE 16

| Ingredients | 0.1% Solution (% w/w) |
|---|---|
| Zinc salt of retinoic acid | 0.1 |
| Butylated hydroxytoluene, N.F. | 0.1 |
| Glycerin | 5.0 |
| Alcohol, 200°, q.s. ad | 100.0 |

EXAMPLE 17

| Ingredients | 0.025% Solution (% w/w) |
|---|---|
| Zinc salt of retinoic acid | 0.025 |
| Butylated hydroxytoluene, N.F. | 0.1 |
| Propylene glycol, U.S.P. | 50.0 |
| Alcohol, SDA 40, q.s. ad | 100.0 |

EXAMPLE 18

| Ingredients | 0.01% Solution (% w/w) |
|---|---|
| Zinc Salt of retinoic acid | 0.01 |
| Butylated hydroxytoluene, N.F. | 0.1 |
| Propylene glycol, U.S.P. | 50.0 |
| Alcohol, SDA 40, q.s. ad | 100.0 |

EXAMPLE 19

| Ingredients | 0.005% Solution (% w/w) |
|---|---|
| Zinc salt of retinoic acid | 0.005 |
| Butylated hydroxytoluene, N.F. | 0.1 |
| Propylene glycol, U.S.P. | 50.0 |
| Alcohol, SDA 40, q.s. ad | 100.0 |

EXAMPLE 20

| Ingredients | 0.2% Cream (% w/w) |
|---|---|
| Zinc salt of retinoic acid | 0.2 |
| Xanthan gum, food grade | 0.3 |
| Polyoxyl 40 stearate | 5.0 |
| Stearic acid | 19.0 |
| Stearyl alcohol | 3.0 |
| Isopropyl myristate | 10.0 |
| Butylate hydroxytoluene | 0.1 |
| Sorbic acid | 0.2 |
| Citric acid | 0.05 |
| Purified water, q.s. | 100.0 |

EXAMPLE 21

| Ingredients | 0.1% Cream (% w/w) |
|---|---|
| Zinc salt of retinoic acid | 0.1 |
| Isopropyl myristate | 10.0 |
| Polyoxyethylene 20 stearyl ether | 2.7 |
| Polyoxyethylene 2 stearyl ether | 0.3 |
| Sperm wax | 5.0 |
| Cetyl alcohol | 2.5 |
| Propylene glycol | 5.0 |
| Glyceryl monostearate | 10.0 |

-continued

| Ingredients | 0.1% Cream (% w/w) |
|---|---|
| Sorbic acid | 0.2 |
| Purified water q.s. ad | 100.0 |

EXAMPLE 22

Comparative performance testing between several concentrations of zinc salt or all-trans-retinoic acid and a positive control comprising retinoic acid was conducted to ascertain efficacy of the zinc salt as a potential acne treating agent. The results, summarized in Table I below, show that, while not as active as retinoic acid at equivalent concentrations in the same vehicle, the zinc salt of retinoic acid did mimic retinoic acid in showing a significant increase in thymidine uptake, a measure of increased DNA synthesis, in this screen for anti-acne activity. Thus, it has been well documented that the topical application of retinoic acid provokes increased DNA synthesis in the epidermis of guinea pigs. Mimicking the effect of retinoic acid on this biological parameter (i.e. DNA synthesis), while it does not guarantee equality in clinical efficacy against acne, is a biological effect which can be measured readily and is considered generally predictive of clinical efficacy.

In these studies, a paired design utilizing each animal as its own control was followed. Male guinea pigs (Hartley strain) weighing ca. 400 g. each were used. The animals were housed singly in wire cages, handled daily during experimentation, provided chow and water ad libitum, and maintained on 12/12 hour light/dark cycles. Prior to the experimental procedure, the animals were maintained as above for three days.

On the first day of the experiment, one ear (dorsal skin) of each animal was randomly selected and treated with 25 λ (0.025 ml) of the experimental solution, and the other ear was treated with an equal volume of the placebo vehicle (control). Ten animals for each group were so treated. These topical applications were made at 9:00 a.m. on the first four days of the experiment. All the animals received chronic administration of tritiated thymidine ($^3$H-TdR) for these first four days. The $^3$H-TdR was given intraperitoneally at ca.9:30 a.m., 1:30 p.m. and 5:00 p.m. of each day (10μCi in 0.1 ml H$_2$O/injection; specific activity - 2.0 Ci/mM). On the fifth day (9:00 a.m.), the animals were killed, and 6 mm diameter punches of ear skin from the central portion of the treated sites were harvested. Each of these tissue samples was solubilized in 1 ml NCS solubilizer at 37°–50°0 C. for 1–3 days. The dissolved tissues, kept in scintillation vials, were acidified with acetic acid (25-50λ), and a simple fluor was added: diphenyloxazole (PPO) and toluene. The radioactivity of the samples was determined by multiple counting on a Beckman LS counter. All cpm values were quench corrected by external standardization to yield dpm/6 mm punch of skin. Quench correction is especially important as some of the samples show faint yellow coloration due to presence of the retinyl derivative, and, therefore, present considerable color quench. Previous studies with retinoic acid have shown that the $^3$H-TdR is found in the epidermis, with only little occurring in the dermis. The treatment groups in these studies were as follows:

| Group | Experimental Ear | Control Ear | N |
|---|---|---|---|
| I | 0.001% Zinc salt of retinoic acid | PG/EtOH* | 10 |
| II | 0.01% Zinc salt of retinoic acid | PG/EtOH | 10 |
| III | 0.05% Zinc salt of retinoic acid | PG/EtOH | 10 |
| IV | 0.05% Retinoic Acid | Pg/EtOH | 10 |

*Propylene glycol/Ethanol = 50/50

The uptake of $^3$H-TdR was greatest in Group IV (Retinoic acid). A dose-related uptake of $^3$H-TdR was seen in Groups I - III treated with zinc salt of retinoic acid. The lowest concentration (Group I, 0.001%) showed no apparent increase in uptake compared to control. Slight increases were apparent in Group II (0.01%), and Group III (0.05%) showed highest uptake for the zinc salt treatments. Daily gradings of erythema subjectively evaluated on a 0-3 scale were made and graphed. Total erythema was expressed by integrating the areas under these response curves. The total erythema correlated with the $^3$H-TdR uptake measurements. These data are summarized in Table I.

TABLE I

| Group | Treatment | DPM ± S.E. | Erythema (Integrated) |
|---|---|---|---|
| I | 0.001% Zinc salt of retinoic acid | 868 ± 79 | 1.9 |
| | PG/EtOH | 961 ± 94 | 1.8 |
| II | 0.01% Zinc salt of retinoic acid | 931 ± 164 | 2.8 |
| | PG/EtOH | 707 ± 74 | 2.1 |
| III | 0.05% Zinc salt of retinoic acid | 1583 ± 173 | 3.6 |
| | PG/EtOH | 1104 ± 116 | 2.4 |
| IV | 0.05% Retinoic Acid | 1805 ± 313 | 3.3 |
| | PG/EtOH | 975 ± 90 | |

EXAMPLE 23

Zinc salt of retinoic acid was evaluated for comedolytic activity in a rabbit ear model system.

Comedo formation was induced by topical administration of 5% coal tar in Polyan ® to both ears of albino rabbits once daily, five consecutive days/week for two weeks. During the following two weeks, one ear was treated topically for five consecutive days/week with 0.5 ml of test solution or gel containing various concentrations of zinc salt of retinoic acid. The contralateral ear of each rabbit served as an untreated control. With the gel vehicle, the contralateral ear was treated with placebo gel. After two weeks treatment, 8 mm punch biopsies of skin from each ear were obtained, examined microscopically, and follicular distension was graded on a 0-3 scale (0=none, 1=slight, 2=moderate, 3=marked). The results of these studies are summarized in Tables II and III.

Table II shows that 0.1% zinc salt gel had a pronounced level of comedolytic activity over placebo gel in the rabbit ear model system. Also, as shown in Table III, in an alcohol/propylene glycol vehicle (50/50, w/w), zinc salt at 0.05% and 0.1% showed good comedolytic activity.

Table II

COMEDOLYTIC ACTIVITY OF ZINC SALT OF RETINOIC ACID GEL

| Treatment | N* | Mean Comedolytic Scores |
|---|---|---|
| 0.1% zinc salt gel (composition of Example 2) | 6 | 0.5 |
| Placebo gel | 6 | 2.3 |

*Number of animals. Paired design. Contralateral ear was treated with placebo gel.

Table III

COMEDOLYTIC ACTIVITY OF ZINC SALT OF RETINOIC ACID SOLUTIONS

| | | Mean Comedolytic Scores | |
|---|---|---|---|
| Treatment | N* | Treated Ear | Untreated Ear |
| 0.05% zinc salt solution (composition of Example 15) | 6 | 1.5 | 2.5 |
| 0.1% zinc salt solution (composition of Example 12) | 6 | 0.8 | 2.7 |

*Number of animals.

EXAMPLE 24

A 28-day topical tolerance study in guinea pigs compared the effects of a 0.1% zinc salt of retinoic acid gel (composition of Example 2) with 0.05% retinoic acid gel or placebo gel (both comprising the vehicle of Example 2) after daily application of 0.05 ml of each test agent to both animal ears. The two active agents were both judged somewhat irritating based on the degree of erythema and scaling produced. Only slight response was elicited by the placebo gel. The 0.05% retinoic acid gel and the 0.1% zinc salt gel were approximately equally irritating. No accommmodation to the agents was observed, although there was some fluctuation in the intensity of the response over the experimental period.

In a 10-day repeat dose skin irritation study, the effects of twice daily application of 0.1% zinc salt gel (Example 2), 0.05% retinoic acid gel or placebo gel to shaved intact or abraded back skin of 16 mature albino rabbits of both sexes were evaluated. 0.1% zinc salt gel was slightly less irritating than retinoic acid gel, and the placebo gel was essentially non-irritating. The rabbits remained in good condition throughout the study. Neither skin abrasion nor sex of the test animal grossly influenced the intensity of local irritation.

A third study appraised the primary skin irritation elicited by 0.1% zinc salt gel (formula of Example 2), 0.05% retinoic acid gel and the placebo gel on the denuded intact or abraded backs of mature male albino rabbits. The compounds were allowed to remain under occlusive dressing for 24 hours; the degree of skin irritation was determined 24 and 72 hours after the application period.

The placebo gel had a mild Primary Irritation Index (1.4), and the two active gels both had moderate Primary Irritation Indices (3.9 and 4.2, respectively).

Variations can, of course, be made without departing from the spirit and scope of the invention.

What is claimed is:

1. A zinc salt of all-trans-retinoic acid having the theoretical structural formula:

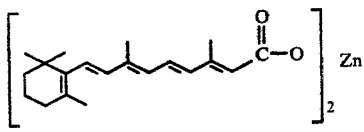

and a zinc content of about 7.1 to 8.5 weight percent.

2. A topical composition for the treatment of acne comprising a therapeutically effective concentration of a zinc salt of all-trans-retinoic acid in a pharmaceutically acceptable topical vehicle compatible therewith, said zinc salt having the theoretical structural formula:

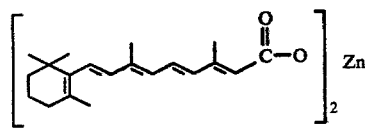

and a zinc content of about 7.1 to 8.5 weight percent.

3. The composition of claim 2 wherein said concentration is from about 0.001% to about 0.5% by weight.

4. The composition of claim 3 wherein said concentration is from about 0.005% to about 0.05% by weight.

5. The composition of claim 3 wherein said concentration is from about 0.01% to about 0.025% by weight.

6. The composition of claim 2 wherein said topical vehicle is an alcoholic gel.

7. The composition of claim 2 wherein said topical vehicle is a liquid.

8. The composition of claim 2 wherein said topical vehicle is a cream.

9. The composition of claim 6 wherein said vehicle consists essentially of an organic solvent selected from the group consisting of ethanol, isopropanol, propylene glycol and mixtures thereof; an effective amount of a pharmaceutically acceptable antioxidant soluble in said organic solvent; and an effective amount of a pharmaceutically acceptable gelling agent solvated in said organic solvent.

10. The composition of claim 9 wherein the gelling agent is selected from the group consisting of hydroxyethylcellulose, hydroxypropyl cellulose, and an acidic carboxy vinyl polymer of high molecular weight.

11. The composition of claim 9 wherein the antioxidant is selected from the group consisting of butylated hydroxyanisole, butylated hydroxytoluene, α-tocopherol, ascorbic acid, and propyl gallate.

12. The composition of claim 10 wherein said carboxy vinyl polymer is neutralized with a pharmaceutically acceptable alkaline material.

13. The composition of claim 9 which contains from about 0.01 to about 0.1% by weight of said antioxidant and from about 0.5 to about 5.0% by weight of said gelling agent.

14. The composition of claim 9 wherein said organic solvent comprises from about 84 to about 99% by weight of said composition.

15. The composition of claim 12 wherein said alkaline material is selected from the group consisting of potassium hydroxide, β-alanine and diisopropanol amine.

16. The composition of claim 9 wherein said organic solvent comprises a mixture selected from the group consisting of ethanol and propylene glycol; isopropanol and propylene glycol; and ethanol and isopropanol.

17. The composition of claim 7 wherein said vehicle comprises a water-miscible organic liquid selected from the group consisting of ethanol, isopropanol, propylene glycol, the liquid polyethylene glycols, the liquid polypropylene glycols, and mixtures thereof.

18. The composition of claim 17 wherein said organic liquid comprises a mixture of ethanol and propylene glycol.

19. The composition of claim 8 wherein said vehicle comprises from about 1.0 to about 10.0% by weight of an emulsifier, from about 15.0 to about 50.0% by weight of a hydrophobic material selected from the group consisting of petrolatum, beeswax, sperm wax, lanolin, mineral oil, liquid and solid fatty acids having from about 12 to about 20 carbon atoms, fatty alcohols having from about 12 to about 20 carbon atoms, and fatty acid esters wherein the fatty acid moiety has from about 12 to about 20 carbon atoms, from about 0.05 to about 1.0% by weight of a preservative, from about 0.01 to about 1.0% by weight of an antioxidant, and water.

20. The composition of claim 19 which further comprises from about 0.1 to about 1.0% by weight of xanthan gum.

21. The composition of claim 19 wherein the emulsifier is selected from the group consisting of polyoxyethylene 25 oxypropylene stearate, polyoxyl 40 stearate, polyethylene glycol 400 monostearate, polyethylene glycol 600 monostearate, polyoxyethylene 20 stearyl ether and polyoxyethylene 2 stearyl ether.

22. The composition of claim 19 wherein the preservative is sorbic acid.

23. The composition of claim 19 wherein the antioxidant is a member selected from the group consisting of butylated hydroxytoluene, and α-tocopherol.

24. The composition of claim 19 wherein the hydrophobic material is selected from the group consisting of a stearyl alcohol, petrolatum, stearic acid, isopropyl myristate, cetyl alcohol, beeswax, sperm wax, lanolin, mineral oil and glyceryl monostearate.

25. The composition of claim 9 further comprising an additive selected from the group consisting of dyes, perfume oils, sunscreens, antimicrobials and topical corticosteroids.

26. The composition of claim 17 further comprising an additive selected from the group consisting of dyes, perfume oils, sunscreens, antimicrobials and topical corticosteroids.

27. The composition of claim 19 further comprising an additive selected from the group consisting of dyes, perfume oils, sunscreens, antimicrobials and topical corticosteroids.

28. A method of treating acne which comprises periodically applying to the affected site the composition of claim 2.

29. The method of claim 28 which comprises applying said composition at regular intervals of from about 7 to about 21 times weekly.

* * * * *